(12) United States Patent
Watanabe et al.

(10) Patent No.: US 8,304,609 B2
(45) Date of Patent: Nov. 6, 2012

(54) ROOT-KNOT NEMATODE-RESISTANCE GENE AND APPLICATION THEREOF

(75) Inventors: Kazuo Watanabe, Ibaraki (JP); Junko Watanabe, Ibaraki (JP)

(73) Assignee: University of Tsukuba, Tsukuba-shi, Ibaraki (JP)

( * ) Notice: Subject to any disclaimer, the term of this patent is extended or adjusted under 35 U.S.C. 154(b) by 2414 days.

(21) Appl. No.: 10/509,420

(22) PCT Filed: Nov. 27, 2002

(86) PCT No.: PCT/JP02/12392
§ 371 (c)(1),
(2), (4) Date: Sep. 24, 2004

(87) PCT Pub. No.: WO03/080838
PCT Pub. Date: Oct. 2, 2003

(65) Prior Publication Data
US 2011/0162102 A1 Jun. 30, 2011

(30) Foreign Application Priority Data
Mar. 27, 2002 (JP) ................. 2002-089622

(51) Int. Cl.
*A01H 5/00* (2006.01)
*C12N 15/82* (2006.01)
*C12N 15/29* (2006.01)
(52) U.S. Cl. ....... 800/302; 536/23.6; 800/279; 800/317; 435/320.1
(58) Field of Classification Search .................. None
See application file for complete search history.

(56) References Cited

FOREIGN PATENT DOCUMENTS

| WO | 99/54490 | | 10/1999 |
|---|---|---|---|
| WO | 99/54490 | A2 | 10/1999 |
| WO | 00/06753 | | 2/2000 |
| WO | 00/06753 | A1 | 2/2000 |
| WO | 00/06754 | | 2/2000 |
| WO | 00/06754 | A2 | 2/2000 |
| WO | WO0006754 | * | 2/2000 |
| WO | 01/29239 | | 4/2001 |
| WO | 01/29239 | A2 | 4/2001 |

OTHER PUBLICATIONS

Milligan et al (1998, Plant Cell 10:1307-1319).*
Rafiqi et al, 2009, Sem. Cell Devel. Biol. 20:1017-1024.*
Guo et al (2004, Proc. Natl. Acad. Sci. USA 101: 9205-9210).*
Japanese Office Action dated Nov. 4, 2008, issued in corresponding Japanese Patent Application No. 2003-578564.
European Office Action dated Jan. 9, 2009, issued in corresponding European Patent Application No. 02783663.4.
European Office Action dated Mar. 28, 2008, issued in corresponding European Patent Application No. 02783663.
Milligan, S. B., et al; "The Root Knot Nematode Resistance Gene Mi from Tomato is a Member of the Leucine Zipper, Nucleotide Binding, Leucine-Rich Repeat Family of Plant Genes"; The Plant Cell, vol. 10, pp. 1307-1319, Aug. 1998.
Ea van der Vossen et al.; Plant J., vol. 23, No. 5, pp. 567-576, 2000. Cited in the PCT search report.
A. Bandahmane et al.; Plant Cell, vol. 11, No. 5, pp. 781-792, 1999. Cited in the PCT search report.
A. Bendahmane et al.; Plant J. , vol. 21, No. 1, pp. 73-81, 2000. Cited in the PCT search report.
Om de Ilarduya et al.; Plant J., vol. 27, No. 5, pp. 417-425, 2001. Cited in the PCT search report.
Ea van der Vossen et al.; Plant J., vol. 23, No. 5, pp. 567-576, 2000.
A. Bendahmane et al.; Plant Cell, vol. 11, No. 5, pp. 781-791; 1999.
A. Bendahmane et al.; Plant J., vol. 21, No. 1, pp. 73-81, 2000.
O.M. de Ilarduya et al.; Plant J., vol. 27, No. 5, pp. 417-425, 2001.
J.C. Veremis and P.A. Roberts, "Relationships between Meloidogyne incognita resistance genes in *Lycopersicon peruvianum* differentiated by heat sensitivity and nematode virulence", Theor Appl Genet, vol. 93, 1996, 950-959, Dept. of Nemalology Univ. of CA, Riverside, CA.
J. Yaghoobi, I, Kaloshian, Y. Wen and V.M. Williamson, "Mapping a new nematode resistance locus in *Lycopersicon peruvianum*", Theor Appl Genet, 9195, 457-464, Yaghoobi and Williamson (Center for Eng. Plants for Resistance Against Pathogens, CA) and Kaloshian, Wen and Williamson (Dept. of Nematology, CA) 1995.

* cited by examiner

*Primary Examiner* — Anne Kubelik
(74) *Attorney, Agent, or Firm* — Westerman, Hattori, Daniels & Adrian, LLP

(57) ABSTRACT

This invention relates to an excellent root-knot nematode-resistance gene and a method for using the same. More particularly, this invention relates to a novel root-knot nematode-resistance gene that is unaffected by high temperature and is applicable to and quantitatively resistant to a wide variety of root-knot nematode species and strains and a root-knot nematode-resistant transgenic plant into which such gene has been introduced.

7 Claims, 4 Drawing Sheets
(2 of 4 Drawing Sheet(s) Filed in Color)

2A  Primer: RKN

2B  Primer: Start2 x 2, PotaLRR

3A: Recombinant

3B: Control

3C: TA209

4A: Recombinant

4B: Control

ROOT-KNOT NEMATODE-RESISTANCE GENE AND APPLICATION THEREOF

TECHNICAL FIELD

The present invention relates to a novel root-knot nematode-resistance gene. More particularly, the present invention relates to a novel root-knot nematode-resistance gene that is unaffected by high temperature and is applicable to and quantitatively resistant to a wide variety of root-knot nematode species and strains. Further, the present invention relates to a method for using such gene.

BACKGROUND ART

Nematodes are animal species that constitute a large phylum and are a type of harmful organisms parasitizing plants or animals. In general, root-knot nematodes parasitizing plants are 1 mm or shorter in length. However, they absorb nourishment from plant cell cytoplasms, and the damage caused thereby represents as much as approximately one billion dollars per year worldwide. Up to the present, approximately 70 species of root-knot nematodes belonging to the genus *Meloidogyne* have been identified. Since they parasitize all types of crops and a wide variety of weeds, they are reported to adversely affect over 2,000 plant species, including sweet potatoes, tomatoes, and Irish potatoes.

When a plant is infected with root-knot nematodes, no distinctive symptom that would be effective for determining parasitism at the initial stage is observed in the aerial part; however, a gall or knot begins to form below the ground. The size of such gall or knot varies depending on the species or variety thereof, and is approximately 1 to 2 mm in many cases. Thus, such gall or knot is sometimes difficult to visually observe, although egg masses laid on the surface of the gall or knot or on roots can be visually observed. The most significant symptom is a vertical crack appearing on the root or tuber, and nematodes at various developmental stages parasitize the infected root or tuber. Root-knot nematode infection not only lowers crop yields but also drastically reduces or eliminates the market value of the infected root or tuber. Also, a crack created on a root or tuber allows other pathogenic organisms to easily attack the plant, which in turn increases the likelihood of complex infection (Hooker, W. J., Compendium of Potato Diseases, pp. 97-98, 1981, The American Phytopathological Society, St. Paul Minn., U.S.A.; Jansson & Raman, Sweet Potato Pest Management, pp. 1-12, 1991, Westview Press, Boulder, Colo., U.S.A.; Jones et al., Compendium of Tomato Diseases, pp. 49-50, 1991, APS PRESS, St. Paul, Minn., U.S.A.).

Nematodes of the genus *Meloidogyne* parasitizing potatoes are of the following four species: *Meloidogyne (M.) arenaria* Chitwood; *M. incognita* Chitwood; *M. hapla* Chitwood; and *M. javanica* Chitwood. Among them, the *Meloidogyne incognita* nematode is generated with the highest frequency in potato fields worldwide (Hooker, W. J., Compendium of Potato Diseases, pp. 97-98, 1981, The American Phytopathological Society, St. Paul, Minn., U.S.A.). Nematode infection is observed in potato cultivating areas in Kyushu, Japan, where the weather is warm. Accordingly, conferment of resistance upon crops or development of integrated pest control techniques is desired.

In the case of potatoes, root-knot nematodes have been controlled for a long time via crop rotation. This technique is effective in terms of reduction of the population density of nematodes; however, control of root-knot nematodes simply via crop rotation is difficult in the case of omnivorous root-knot nematodes due to limitations concerning the cycle of crop rotation. Alternatively, the population density of root-knot nematodes can be restricted with the aid of ammonia nitrogen by adding organic fertilizers. This technique is still employed in Africa, Asia, and Central and South America at present, although it is not an ultimate method of control of root-knot nematodes. Soil fumigation with dichloropropene, methyl bromide, or the like is the best technique in terms of speed of action. This technique, however, adversely affects the ecosystem and farmers.

Currently, a technique for enhancing the nematode resistance of host potatoes has been experimentally carried out, and a variety of resistant lines have been created (Watanabe et al., Amer. Potato J. 71: 599-604, 1994; Watanabe et al., Breeding Science 45: 341-347, 1995; Watanabe et al., Breeding Science 46: 329-336, 1996; Watanabe et al. Breeding Science 49: 53-61, 1999; Watanabe & Watanabe, Plant Biotechnology 17: 1-16, 2000). Tetraploid potato cultivars that are highly resistant to nematodes, particularly to *Meloidogyne incognita*, have not yet been created.

Conferment of resistance using root-knot nematode-resistant diploid wild relatives upon cultivated potatoes has been attempted. Based on genetic analysis of phenotypes or breeding experiments, diploid wild relatives have been found to comprise root-knot nematode-resistance genes (Rmi), and these genes have been found to have quantitative resistance with additive effects (Iwanaga et al., J. Amer. J. Hort Sci., 114 (6): 1008-1113, 1989; Watanabe et al., Breeding Sci., 46: 323-369, 1996; Watanabe et al., Breeding Sci., 49: 53-61, 1999). In the aforementioned literature, resistance induced by such Rmi genes is reported to be unaffected by temperature and to be active at high temperatures. The Rmi is, however, not yet isolated, and the sequence thereof is not yet known. Since cultivated potatoes are autotetraploids, the heredity patterns thereof are complicated. Thus, the breeding of a useful resistant variety has not yet been realized.

At present, the positions of a group of genes resistant to the genus *Meloidogyne* on several gene maps have only been verified regarding tomatoes and potatoes. In the case of tomatoes, for example, the *Lycopersicon. peruvianum*-derived Mi gene resistant to *Meloidogyne incognita* Chitwood, *Meloidogyne javanica* Chitwood, and *Meloidogyne arenaria* Chitwood is reported to be located on chromosome 6 (Messeguer et al., Theor. Appl. Genet., 82: 529-536, 1991; Ho et al., Plant J., 2: 971-982, 1992). The *L. peruvianum*-derived Mi3 gene resistant to *Meloidogyne incognita* Chitwood and *Meloidogyne javanica* Chitwood is also reported to be located on chromosome 12 (Yaghoobi et al., Theor. Appl. Genet., 91: 457-464, 1995). The Mi gene was isolated by the group of Williamson et al., and the constitution thereof has been elucidated (Rossi et al., Proc Natl Acad. Sci, 95: 9750-9754, 1998; Milligan et al., Plant Cell, 10: 1307-1319, 1998). Since the Mi gene is affected by high temperature, the resistance thereof becomes disadvantageously inactive upon exposure to high temperatures during the initial stage of infection, i.e., 24 to 48 hours after infection.

In the case of potatoes, Rmc1 resistant to the *Meloidogyne chitwoodi* race 1 is reported to be located on chromosome 11 of *S. bulbocastanum* (Brown et al., Theor Appl. Genet., 92: 572-576, 1996). Concerning transmission of resistance to *Meloidogyne incognita* Chitwood, the following two possibilities have been pointed out: 1) two or more genes may be involved with resistance (Gomez et al., Amer. Potato J., 60: 353-360, 1983); and 2) cytoplasm may be involved with development of resistance (Gomez et al., Amer. Potato J., 60: 353-360, 1983; Iwanaga et al., J. Amer. Hort. Sci., 114: 1108-1013. 1989). Further, resistance to *Meloidogyne incognita*

Chitwood is found to be additive and quantitative resistance that is controlled by 5 or 6 resistance genes (Watanabe et al., Breed. Sci., 9: 53-61, 1999; Watanabe et al. submitted).

In general, potent resistance of plants to pathogens is often very highly specific. The "gene-for-gene" hypothesis proposed by Flor (Flor, Ann. Rev. Phytopathol., 9: 275-296, 1971) describes such highly specific resistance based on the interaction between resistance genes of plants and avirulence genes of pathogens. It is generally hypothesized that a ligand-receptor model is a mechanism for gene-for-gene molecule recognition (Gabriel & Rolfe, Ann. Rev. Phytopathol. 28: 365-391, 1990).

Up to the present, the isolated resistance genes are classified into 5 groups based on functional or structural similarities of gene products (Baker et al., Science, 276: 726, 1997; Bergelson et al., Science 292: 2281-2285, 2001; Dangl and Jones, Nature 411: 826-833, 2001). The resistance genes classified as class I have nucleotide-binding sites (NBS) and leucine-rich repeats (LRR), and it is deduced that these regions are involved with signal transduction for developing resistance. Examples of the isolated genes classified as class I include: the N gene of tobacco resistant to tobacco mosaic virus (Whitham et al., Cell, 78: 1101-1105, 1994); the L6 (Lawrence et al., Plant Cell, 7: 1195-1206, 1995) and M (Anderson et al., Plant Cell, 9: 641-651, 1997) genes of flax resistant to *Melampsora lini*; the RPP5 (Bent, Plant Cell, 8: 1757-1771, 1996) gene of *Arabidopsis thaliana* resistant to *Peronospora parasitica*, the RPS2 (Bent et al., Science 265: 1856-1860, 1993; Mindrinos et al., Cell, 78: 1089-1099, 1994) and the RPM1 (Grant et al., Science, 269; 843-846, 1995) genes thereof resistant to *Pseudomonas syringae*; and the PRF (Salmeron et al., Cell 86: 123-133, 1996) gene of tomatoes resistant to *Pseudomonas syringae* and the I2C-1 (Ori et al., Plant Cell 9: 521-531, 1997) gene thereof resistant to *Fusarium oxysporum*. Further, the aforementioned *L. peruvianum*-derived Mi gene of tomatoes resistant to root-knot-nematodes is also found to have NBS and LRR (Milligan et al., Plant Cell 10: 1307-1319, 1998).

A protein belonging to class I has incomplete LRR on its C-terminal side and NBS on its N-terminal side. NBS is observed in ATPase, GTPase, and the like, and is constituted by 3 motifs including a P loop (Traut, Eur J. Biochem., 229: 9-19, 1994). In general, the first kinase 1a domain forms a phosphoric acid-binding loop, and the kinase 2 domain is located downstream thereof. Aspartic acid immobilized in the kinase 2 domain is deduced to adjust a metal-binding site that is necessary for migration of phosphoric acid. The kinase 3a domain located further downstream thereof has tyrosine or arginine that often interacts with purine in ATP (Traut, Eur J. Biochem., 229: 9-19, 1994). Existence of such NBS indicates that kinase activity or the G-protein plays a key role in activating resistance (Hammond-Kosack & Jones, 1997, Annu. Rev. Plant Phusiol. Plany Mol. Bioi., 48: 575-607, 1997).

The LRR domain is observed in a variety of proteins, and it is considered to be often involved with protein-protein interactions in yeast, *Drosophila*, human, or other species (Kobe & Deisenhofer, Nature, 366: 751-756, 1993). Concerning plant resistance to pests, however, it is deduced that the LRR domain functions as a ligand-binding domain produced from avirulence (Avr) genes or facilitates interactions between the products of resistant (R) genes and other proteins involved with defense signal transduction (Bent, Plant Cell, 8: 1757-1771, 1996).

Potatoes are major crops worldwide, and they are excellent crops that are compatible with a wide range of production systems from high-input agriculture conducted in developed countries such as the U.S.A. and Japan to low-input agriculture conducted in developing countries in Africa, Asia, and Latin America. Potatoes are extensively cultivated for applications such as feeds, industrial starch, and fermentation material as well as for food such as staple food, vegetables, or snacks worldwide (Harris, P. M. The Potato Crop, Chapman and Hall, London, 1978; International Potato Center http://www.cgiar.org.cip/2004). From the viewpoint of the amount of production and calorie supply, potatoes are one of the most important crops particularly in developing countries. In these countries where the populations are drastically increasing, an increased amount of production and productivity of potatoes will be further expected for this valuable food source in years to come.

A large amount of potatoes produced have been lost due to pests, and damage caused by root-knot nematodes has been particularly serious in extensive areas covering tropical, subtropical, and temperate regions (Hooker, W. J., Compendium of Potato Diseases, pp. 97-98, 1981, The American Phytopathological Society, St. Paul Minn., U.S.A.).

Unfortunately, there is no ultimate solution for the damage caused by root-knot nematodes, and thus, elucidation of functions and structures of resistance genes has been awaited.

DISCLOSURE OF THE INVENTION

An object of the present invention is to provide a solution for serious damage caused by root-knot nematodes by discovering an excellent root-knot nematode-resistance gene that is extensively applicable to a variety of root-knot nematode species.

The present inventors have screened diploid potato lines based on nucleotide sequences such as NBS or LRR that are common among a group of plants' resistance genes. As a result, they have succeeded in isolating a novel gene having excellent root-knot nematode resistance. They have also succeeded in producing excellent root-knot nematode-resistant transgenic plants via utilization of the aforementioned gene, thereby completing the present invention.

Specifically, the present invention relates to the following (1) to (8).

(1) A gene consisting of the following DNA (a) or (b):
   (a) DNA consisting of the nucleotide sequence as shown in SEQ ID NO: 1; or
   (b) DNA hybridizing under stringent conditions to DNA consisting of a nucleotide sequence complementary with the DNA consisting of the nucleotide sequence as shown in SEQ ID NO: 1 and conferring root-knot nematode resistance upon a host.

(2) The gene according to (1), wherein the root-knot nematode resistance is quantitative resistance where the level of resistance increases depending on the number of gene copies.

(3) A recombinant vector comprising the gene according to (1).

(4) A transformant obtained by introducing the gene according to (1) into a host.

(5) The transformant according to (4), wherein the host is a plant.

(6) The transformant according to (5), wherein the plant is of the Solanaceae family.

(7) A method for producing a root-knot nematode-resistant transgenic plant by introducing the gene according to (1) into the plant.

(8) An agent for root-knot nematode control comprising the gene according to

1. Novel Root-Knot Nematode-Resistance Gene (1) Characteristics of the Gene According to the Present Invention The gene according to the present invention is a novel root-knot nematode-resistance gene isolated from a diploid potato line. This gene differs from conventional root-knot nematode-resistance genes in the following respects:

(i) unlike a single dominant root-knot nematode-resistance gene such as a resistance gene of a tomato (the Mi gene), the gene according to the present invention has "quantitative resistance" where the degree of resistance is enhanced in accordance with the number of gene copies;

(ii) unlike the resistance gene of a tomato, resistance breakdown does not occur because of high-temperature sensitivity; and (iii) the gene according to the present invention can be extensively applied to a wide variety of root-knot nematode species and strains.

(2) Isolation of the Gene According to the Present Invention

The gene according to the present invention can be screened from genomic DNA or a cDNA library of the diploid potato genotype 85.37.38 that is known to have a root-knot nematode-resistance gene (Watanabe et al., Amer. Potato J. 71: 599-604, 1994) based on sequence information such as NBS or LRR that is common among a group of plants' resistance genes. For example, primers may be designed from a domain conserved in known plants' genes resistant to pests, such as a NBS or LRR sequence, based on the general theory of Hammond-Kosack and Jones (Ann. Rev. Plant Physiol. Plan Mol. Biol. 48: 575-607, 1997) or the like. These primers may be used to amplify the gene of interest isolated from the aforementioned cDNA library of the diploid potato line.

(3) Nucleotide Sequencing

The nucleotide sequence of the obtained gene can be determined in accordance with a conventional technique. Nucleotide sequencing may be carried out by a conventional technique, such as chemical modification developed by Maxam & Gilbert, dideoxynucleotide chain termination utilizing an M13 phage, or a method utilizing an automated nucleotide sequence analyzer (e.g., ABI PRISM 377 DNA Sequence System, Perkin-Elmer).

SEQ ID NO: 1 represents the nucleotide sequence of the root-knot nematode-resistancegene according to the present invention that has been identified in the aforementioned manner. The root-knot nematode-resistance gene according to the present invention is not limited to the above sequence. It also includes a gene that can hybridize under stringent conditions to a compliment of a gene consisting of the nucleotide sequence as shown in SEQ ID NO: 1 as long as the root-knot nematode resistance, which is characteristic of the gene according to the present invention as described in (1), can be conferred upon a host. Under stringent conditions, for example, a sodium concentration is between 10 mM and 300 mM and temperature is between 25° C. and 70° C. Preferably, the sodium concentration is between 50 mM and 100 mM and the temperature is between 42° C. and 55° C.

If the nucleotide sequence of the gene according to the present invention is once determined, the gene according to the present invention can be further obtained via chemical synthesis, PCR using cDNA or genomic DNA of the present gene as a template, or hybridization using a DNA fragment having each nucleotide sequence as a probe.

2. Vector

The present invention provides a recombinant vector comprising the gene according to the present invention. The gene according to the present invention is introduced into a suitable vector, such as a plasmid, in such a manner that it is maintained unchanged, digested with a suitable restriction enzyme, or ligated to a suitable linker to prepare the aforementioned recombinant vector. Examples of such vector include pUC vectors such as pUC18, pUC19, pUC118, and pUC119 and binary vectors such as pBI101, pBI121, and pGA482. In particular, when an Agrobacterium binary vector is used, a foreign gene is inserted between border sequences of the binary vector, and this recombinant vector is amplified in E. coli. Subsequently, the amplified recombinant vector is introduced into, for example, Agrobacterium tumefaciens LBA4404, EHA101, EHA105, or C58C1Rif$^R$, via freeze thawing, electroporation, or other means. The resultant is used as a transformation vector.

In order to allow a foreign gene to express in a host, a promoter and a terminator need to be located in front of and behind the gene, respectively. Any promoter and terminator can be used without particular limitation as long as they can function in a host. When a plant is a host, examples of a promoter sequence include cauliflower mosaic virus (CaMV)-derived 35S transcript (The EMBO J. 6: 3901-3907, 1987), maize ubiquitin (Plant Mol. Biol. 18: 675-689, 1992), nopaline synthase (NOS) gene, and octopine (OCT) synthase gene promoters. Examples of a terminator sequence include cauliflower mosaic virus-derived and nopaline synthase gene-derived terminators.

In order to more effectively select the transformant of interest, an effective selection marker gene is preferably introduced. Examples of the selection marker gene include a kanamycin-resistance-conferring gene, a hygromycin phosphotransferase (htp) gene conferring antibiotic hygromycin-resistance upon a plant, and a phosphinothricin acetyltransferase (bar) gene conferring bialaphos resistance upon a plant. Such selection marker gene and the gene according to the present invention may be incorporated together into a single vector. Alternatively, 2 types of recombinant DNAs independently comprising them in separate vectors may be used.

3. Transformant

The present invention also provides a transformant into which the gene according to the present invention has been introduced. This transformant is produced by transforming a host by using the aforementioned vector according to the present invention. The host is not particularly limited as long as the gene according to the present invention can function therein. It is preferably a plant, and examples thereof include a plant of the Solanaceae family, a plant of the Convolvulaceae family such as sweet potato, and a plant of the Brassicaceae family including root crops such as radish. The gene according to the present invention is considered to be capable of effectively functioning in over 2,000 species of plants. Plants of the Solanaceae family, such as potatoes, tobacco, and tomatoes are particularly preferable. The term "plant" used in the present invention refers to cultured cells of plants, cultivated plants, plant organs (e.g., leaves, flower petals, stems, roots, rhizomes, or seeds), or plant tissues (e.g., epidermis, phloem, parenchyma, xylem, or fibrovascular bundle). When cultured cells of plants, the entirety of the plants, plant organs, or plant tissues are used as hosts, for example, the gene according to the present invention is introduced into a piece of the obtained plant via the Agrobacterium binary vector method, the particle gun method, the polyethylene glycol method, or other method. Thus, a transformant of interest can be obtained. Alternatively, the gene may be introduced into protoplast via electroporation to prepare a transformant.

The transformant into which the gene according to the present invention has been introduced can be selected via screening using a selection marker or analysis of the functions of the gene according to the present invention, i.e., root-knot nematode resistance. The resulting transformant, particularly a transgenic plant, can be propagated by cultivation in a pot filled with soil or vermiculite and by cutting. The thus propagated transgenic plants and all the offspring thereof are within the scope of the transformant according to the present invention as long as they comprise the gene according to the present invention.

4. Root-Knot Nematode-Resistant Transgenic Plant

The transgenic plant into which the root-knot nematode-resistance gene according to the present invention has been introduced has potent resistance to a wide variety of root-knot nematode species. In addition, resistance conferred by the gene according to the present invention is "quantitative resistance," where the degree of resistance is enhanced in accordance with the number of genes introduced. It should be noted that conventional root-knot nematode-resistance genes do not have quantitative resistance. Accordingly, the gene according to the present invention can produce a transgenic plant having more potent root-knot nematode resistance by increasing the number of genes to be introduced.

Root-knot nematode-resistance genes that have been identified up to the present are affected by temperature and lose their resistance upon exposure to a temperature over a given level (the Mi gene is usually deactivated at 28° C.). The transgenic plant according to the present invention, however, can maintain its resistance to root-knot nematodes even when it is cultivated at high temperatures between 33° C. and 35° C. Accordingly, the transgenic plant into which the gene according to the present invention has been introduced can maintain its root-knot nematode resistance in temperate or tropical regions, where temperature is relatively high.

Thus, the present invention can provide a novel root-knot nematode-resistant transgenic plant and a method for producing the same.

5. Others

The gene according to the present invention confers excellent root-knot nematode resistance upon a host, particularly to plants of the Solanaceae family, such as potatoes, tobacco, and tomatoes. Accordingly, such gene and a composition comprising the same can be used as an agent for root-knot nematode control. The gene according to the present invention, a transgenic plant into which such gene has been introduced, and an agent for root-knot nematode control comprising such gene have important effects of containing the damage and improving the productivity of crops in regions where serious damage is caused by root-knot nematodes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
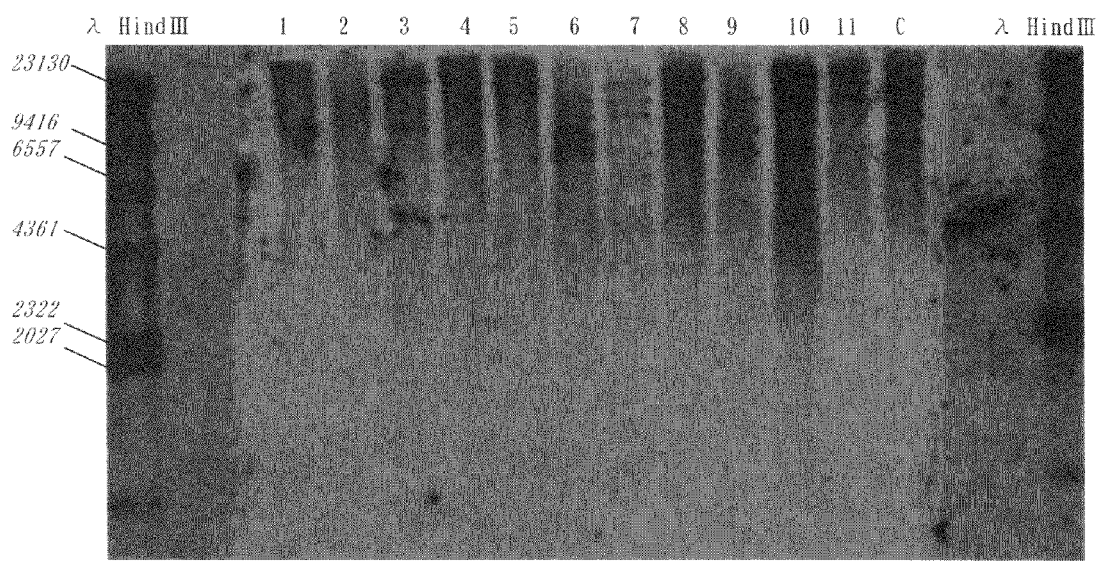
FIG. 1 shows the results of gene introduction confirmed via Southern hybridization.

This description includes part or all of the contents as disclosed in the description of Japanese Patent Application No. 2002-089622, which is a priority document of the present application.

BEST MODES FOR CARRYING OUT THE INVENTION

The present invention is hereafter described in more detail with reference to the following examples, although the technical scope of the present invention is not limited thereto.

Example 1

Isolation of Gene Domain

The following primers were designed from genomic DNA of the diploid potato genotype 85.37.38 known to have resistance genes (Watanabe et al., Amer. Potato J. 71: 599-604, 1994), and the gene was isolated by PCR. The primers were designed from a domain conserved in known plants' genes resistant to pests, such as the sequence NBS or LRR.

```
                                          (SEQ ID NO: 2)
Forward: 5'-GATCCATTCTATAATGTCTCACT-3'

(SEQ ID NO: 3)
Reverse: 5'-CTATCTATAAGATCTTTAATCA-3'
```

The isolated Rmi gene candidate was designated as "Fragment #93," and the total sequence thereof (SEQ ID NO: 1) and homology thereof with known genes were inspected (Table 1).

TABLE 1

| Gene | Homology |
| --- | --- |
| Solanum acaule NBS-LRR protein | 69% |
| Solanum tuberosum RGC | 70% |
| Solanum tuberosum NBS-LRR protein | 69% |
| Solanum tuberosum Disease resistance protein Gpa | 69% |
| Solanum tuberosum Rx protein | 69% |
| Capsicum chacoense disease resistance Protein BS2 | 54% |
| Lycopersicon esculentum Prf protein | 54% |
| Lycopersicon esculentum PRF protein | 52% |
| Lycopersicon pimpinellifolium Prf protein | 53% |
| Lycopersicon esculentum tospovirus resistance protein D protein | 54% |
| Arabidopsis thaliana putative protein | 96% |
| Arabidopsis thaliana RPP13 protein | 48% |
| Arabidopsis thaliana rpp8 protein | 47% |
| Oryza sativa Putative disease resistance protein | 47% |
| Arabidopsis thaliana viral resistance protein | 48% |
| Arabidopsis thaliana disease resistance protein RPM1 isolog | 48% |
| Arabidopsis lyrata NBS/LRR disease resistance protein RPM1 protein | 51% |
| Brassica napus disease resistance gene homolog 9N protein | 49% |
| Oryza sativa RPR1h protein | 47% |
| Oryza sativa RPR1 protein | 46% |
| Brassica napus disease resistance protein | 48% |
| Triticum aestivum stripe rust resistance protein Yr10 protein | 53% |
| Triticum aestivum stripe rust resistance protein Yr10 protein | 52% |
| Oryza sativa Pi-b protein | 86% |
| Oryza sativa Pib protein | 56% |
| Fusarium oxysporum protein | 50% |

A foreign gene was inserted between border sequences of the binary vector, and the resulting recombinant vector was amplified in E. coli. Subsequently, the amplified recombinant vector was introduced into, for example, *Agrobacterium tumefaciens* LBA4404, EHA101, EHA105, or C58C1Rif$^R$, via freeze thawing, electroporation, or other means. The resultant was used for producing a transgenic plant.

Example 2

Construction of Vector (1) Insertion into Binary Vector

The isolated Rmi gene candidate (Fragment #93) was cleaved with BamHI, ligated to the pTarget vector once, cleaved with BamHI again, and then ligated to a binary vector pBE2113Not. The resulting recombinant vector was introduced into *E. coli* DH5α and amplified therein to obtain a vector for *Agrobacterium* introduction (PotatoRKN: pBE2113NotI).

(2) Electroporation

The binary vector (PotatoRKN: pBE2113NotI) was introduced into the *Agrobacterium tumefaciens* LB4404 strain (Gibco BRL) via electroporation. Specifically, the *Agrobacterium tumefaciens* LB4404 strain stored at −80° C. was thawed on ice, and approximately 20 µl thereof was transferred to a 1.5-ml Eppendorf tube under clean bench conditions. DNA (100 ng/µl, 1 µl) was added thereto, the mixture was allowed to stand on ice, and the resultant was then transferred to a cuvette for electroporation.

(3) Confirmation of Gene Introduction

Subsequently, 50 µl of YM medium was added, suctioned, and transferred to a 15-ml Falcon tube. YM medium was further added to bring the total amount to 1 ml, and shaking culture was carried out at 225 ppm and 30° C. for 3 hours. Three hours thereafter, 200 µl of the culture product was spread on kanamycin-containing YM agar medium, culture was carried out at 30° C. for 48 to 56 hours, and the generated colony was subjected to PCR and DNA sequencing to confirm gene introduction.

(4) Colony PCR

The colony of the *Agrobacterium tumefaciens* LBA4404 strain, gene introduction into which had been verified, was removed, and colony PCR was conducted using the reaction solution having the composition as shown in Table 2. The resulting PCR product (1 µl) was removed and then mixed with a small amount of blue juice. The mixture was then electrophoresed in a gel comprising 2% of agarose dissolved in 0.5% TAE. A λ Hind III marker (Marker II, Boehringer Mannheim) was used. Thereafter, a solution having the composition as shown in Table 2 was poured into 8-strip tubes, and the tubes were mounted on the PCR apparatus (GeneAmp 9600, Perkin-Elmer).

TABLE 2

| Substance | Amount required |
|---|---|
| Buffer × 10 | 2.50 µl |
| MgCl$_2$ (150 mM) | 0.5 µl |
| dNTP × 10 | 2 µl |
| Forward primer (PoMi-F-1, 1 pmol/µl) | 2.5 µl |
| Reverse primer (PoMi-R-1, 1 pmol/µl) | 2.5 µl |
| Taq polymerase (10 U/µl) | 0.25 µl |
| Template | Arbitrary |
| dH$_2$O | +α |
| Total | 25 µl |

The above reaction solution was transferred to a 1.5-ml Locking Tube, and 80 µl of 75% isopropanol was added thereto, followed by mixing. The resulting mixture was then allowed to stand at room temperature for 15 minutes and centrifuged for 20 minutes (at room temperature and the maximal rate). The supernatant was removed therefrom, and 250 µl of 75% isopropanol was further added, followed by mixing. Thereafter, the mixture was centrifuged for 5 minutes (at room temperature and the maximal rate), the supernatant was removed, and the centrifugation product was dehydrated in a draft chamber. Subsequently, 25 µl each of the template suppression reagent (TSR) was added and mixed, the mixture was spun down, and heat shock was applied in a Heat Block at 95° C. for 3 minutes. The resultant was allowed to stand on ice and then transferred to a DNA sequencing 310-specific tube. DNA sequencing was then carried out.

The colony of the *Agrobacterium tumefaciens* LB 4404 strain, gene introduction into which had been verified, was removed, and the colony was subjected to shaking culture in YEB medium containing 100 mg/l of kanamycin at 30° C. and 225 rpm overnight. The solution of cultured cells (850 µl each) was poured into cryotubes on ice, 150 µl of glycerin was added, the tubes were sealed and wrapped with Parafilm, and the contents of the tubes were mixed using a vortex mixer. The resultant was wrapped in plastic wrap and then immersed in 99.5% ethanol, which had been cooled to −20° C., and then allowed to cool in a freezer at −20° C. for approximately 10 minutes. Thereafter, the resultant was stored in a storage case which had been cooled to −80° C.

Example 3

Production of Transgenic Plant

A transgenic plant into which a domain of the root-knot nematode-resistance gene has been introduced using the vector prepared in Example 2 was produced. Diploid *Nicotiana benthamiana* (a plant of the Solanaceae family), which is redifferentiated and grown at the early stage and is nematode-sensitive, was used as a host plant. In parallel therewith, the gene was introduced into the nematode-sensitive tetraploid potato variety, Desiree.

(1) Infection of Plant with *Agrobacterium tumefaciens*

The *Agrobacterium tumefaciens* LB4404 strain prepared in Example 2 was allowed to thaw on ice. YEB medium (40 ml) was transferred to 50-ml Falcon tubes under clean bench conditions, and antibiotics were added thereto, followed by mixing in the reverse order. The resulting mixture was poured into the tubes in amounts of 10 ml per tube. The *Agrobacterium tumefaciens* LBA4404 strain (10 W) was added thereto, the resultant was cultured in a shake culture apparatus overnight (at 28° C. and 225 rpm), and the absorbance of the culture solution at 600 nm was assayed using a spectrophotometer. Since the absorbance at this time was approximately 2, the culture solution was diluted with the aid of YEB medium to bring the absorbance to a level between 0.6 and 0.8.

A plant 2 to 3 weeks after subculturing was marked with a surgical scalpel on sterilized filter paper, divided into the root, stem, and leaf portions, and then immersed in sterilized water to prevent drying. The marked plant fragment was immersed in a solution of *Agrobacterium tumefaciens* adjusted to have absorbance between 0.6 and 0.8 for 7 minutes, transferred onto sterilized filter paper, thoroughly drained, and then cultured in a co-culture medium for 3 days. The co-culture medium used herein contained 1 mg/l of benzyladenine (BA), 35 mg/l of trans-zeatin riboside, and 0.1 mg/l of indoleacetic acid.

(2) Subculturing to Co-Culture Medium

As with the case of the section above, a co-culture medium was prepared, 20 ml thereof was poured into each petri dish, sterilized round filter paper was placed thereon, and the infected plant was transferred thereto, followed by culturing for 3 days.

TABLE 3

Composition of modified MS medium: 30 g of sucrose was added to the following composition to bring the amount thereof to 1 liter, the pH level thereof was adjusted to 5.9 with KOH or HCl, and 2.5 g of Gellan gum was then added thereto.

| Sol No. | Component | Substance | Final concentration | Concentration of solution |
|---|---|---|---|---|
| Sol 1 | $NH_4NO_3$ | Ammonium nitrate | 1,650 mg | 82.5 g/l |
| (20 ml/l) | $KNO_3$ | Potassium nitrate | 1,900 mg | 95.0 g/l |
|  | $CaCl_2\ 2H_2O$ | Calcium chloride dihydrate | 440 mg | 22.0 g/l |
| Sol 2 | $MgSO_4\ 7H_2O$ | Magnesium sulfate heptahydrate | 370 mg | 37.0 g/l |
| (10 ml/l) | $KH_2PO$ | Potassium dihydrogen-phosphate | 170 mg | 17.0 g/l |
| Sol 3 | $Na_2EDTA\ 2H_2O$ | Disodium dihydrogen ethylenediamine tetraacetate dihydrate | 37.3 mg | 1.87 g/l |
| (20 ml/l) | $FeSO_4\ 7H_2O$ | Iron (II) sulfate heptahydrate | 27.8 mg | 1.39 g/l |
| Sol 4 | $H_3BO_3$ | Boric acid | 6.2 mg | 620 mg/l |
| (10 ml/l) | $MnSO_4\ 4H_2O$ | Manganese (II) sulfate tetrahydrate | 22.3 mg | 2,230 mg/l |
|  | $ZnSO_4\ 7H_2O$ | zinc sulfate heptahydrate | 8.6 mg | 860 mg/l |
|  | KI | Potassium iodide | 0.83 mg | 83 mg/l |
|  | $Na_2MoO_4\ 2H_2O$ | Sodium molybdate | 0.25 mg | 1 ml/l |
|  | $CuSO_4\ 5H_2O$ | Copper (II) sulfate pentahydrate | 0.025 mg | 1 ml/l |
|  | $CoCl_2\ 6H_2O$ | Cobalt (II) chloride hexahydrate | 0.025 mg | 1 ml/l |
| Sol 5 | Thiamine-HCl | Vitamin B1 hydrochloride | 0.5 mg | 50 mg/l |
|  | Myo-inositol | myo-inositol | 0.1 mg | 10 g/l |
|  | Pyridoxin | Pyridoxine hydrochloride | 0.5 mg | 50 mg/l |
| (10 ml/l) | Nicotinic acid | Nicotinic acid | 5 mg | 500 mg/l |
|  | Glycine | Glycine | 2 mg | 200 mg/l |
|  | Biotin | D-biotin | 0.05 mg | 5 mg/l |
|  | Folic acid | Folic acid | 0.5 mg | 50 mg/l |

(3) Subculturing to Callus-Forming Medium

A callus-forming medium was prepared by adding 1 mg/l of benzyladenine, 0.1 mg/l of NAA, 150 mg/l of kanamycin, and 200 mg/l of carbenicillin to the modified MS medium as shown in Table 3. The prepared medium was poured into petri dishes in amounts of 20 ml per dish. The plant fragments that had been cultured in a symbiotic medium for 3 days were successively subcultured in the aforementioned callus-forming medium.

(4) Subculturing to Shoot-Growing Medium

A shoot-growing medium was prepared by adding 150 mg/l of kanamycin and 200 mg/l of carbenicillin to the modified MS medium as shown in Table 3, and the prepared medium was poured into petri dishes in amounts of 20 ml per dish. The plant fragments that had been cultured in callus-forming medium for approximately 2 weeks where a callus had been formed were successively subcultured in the aforementioned shoot-growing medium. Culture was then carried out in a room lit by light (fluorescent light) all day long.

(5) Subculturing to MS Medium-Containing Test Tubes

The modified MS medium as shown in Table 3 was poured into test tubes in amounts of 5 ml per tube, and the tubes were sterilized in an autoclave. Among the plants that had been redifferentiated in a shoot-growing medium, the plants that had become completely independent were subcultured as a single line in the sterilized test tubes.

(6) Subculturing to Rooting Medium

Kanamycin (75 mg/l) and 100 mg/l of carbenicillin were added to the modified MS medium as shown in Table 3, and the resultant was poured into culture bottles in amounts of 40 ml per bottle to prepare a rooting medium. Plants that had reached a size of 2 to 3 cm after 1 to 2 weeks of culture in the MS medium-containing test tubes were successively subcultured in the aforementioned rooting medium in quantities of approximately 3 plants per bottle.

(7) Conditioning

Commercially available vegetable soil was placed in a planter, culture was carried out in a rooting medium for approximately 3 weeks, and plants, the roots of which had matured, were transferred thereto and grown therein.

Example 4

Confirmation of Gene Introduction Via Southern Hybridization

The regenerated plants were grown in a selection medium, i.e., a kanamycin-containing medium, and rooting-based growth was employed as an indicator to select a line with good growing conditions as a provisional candidate for the transgenic plant. This candidate for the transgenic plant was subjected to Southern hybridization to confirm gene introduction.

(1) Testing Method

DNA of the aforementioned provisional candidate line for the transgenic plant was extracted, and PCR was carried out using primers (SEQ ID NOs: 2 and 3) used in Example 1 to amplify a domain of the root-knot nematode-resistance gene.

The line, introduction of a gene domain into which had been verified via PCR, was subjected to Southern hybridization using the sequence of Rmi (SEQ ID NO: 1) determined in Example 1 as a probe, and the number of genes introduced was estimated. The hybridization conditions are shown in Table 4.

TABLE 4

| Step | Condition | Time |
|---|---|---|
| Baking | 80° C. | 2 hours |
| Prehybridization | 55° C. | 4 hours |
| Hybridization | 55° C. | 17 hours |

TABLE 4-continued

| Step | Condition | Time |
| --- | --- | --- |
| Primary washing | 55° C. | 10 min × 2 |
| Secondary washing | Room temperature | 5 min × 2 |
| Exposure | Dark | 3 hours |

(2) Results

According to the results shown in FIG. 1, positive reactions were also observed in the control. These positive reactions were considered to occur because the control gene had a homologous domain which hybridizes to a non-transgenic plant. Therefore, plants having bands with conditions different from those of the control and having a larger number of bands than the control were determined to be plants into which genes have been introduced.

Example 5

Confirmation of Gene Introduction Via RT-PCR (1) Testing Method
1) Synthesis of cDNA Plants were ground to powder using liquid nitrogen in a mortar and mRNA was extracted in accordance with a conventional technique. Reverse transcription of the mRNA was conducted using the reaction composition as shown in Table 5 and primers prepared by adding dT to random 9 mer and M13 primer M4 attached to the Takara RNA PCR Kit (Takara) to synthesize cDNA. The primers used and the reaction conditions are as shown below.

TABLE 5

| Reaction composition for reverse transcription | |
| --- | --- |
| MgCl$_2$ | 4 ul |
| 10x RNA PCR buffer | 2 ul |
| dNTP mixture | 2 ul |
| RNase inhibitor | 0.5 ul |
| Reverse transcriptase | 1 ul |
| Random 9 mers or oligo dT-adaptor primer | 1 ul |
| Template mRNA | 9.5 ul |
| Total | 20 ul |

<Reaction Utilizing Random 9 Mers Primer>
Random 9 mer: dp(5'-NNNNNNNNN-3')
Reaction conditions: preincubation at 30° C. for 10 minutes; a cycle of 42° C. for 30 minutes, 99° C. for 5 minutes, and 55° C. for 5 minutes
<Reaction Utilizing Oligo dT-Adaptor Primer>
Primers prepared by adding Oligo-dT to the oligo-dT adaptor: M13 primer M4 5'-gttttcccagtcacgac-3' (SEQ ID NO: 4) was used.
Reaction conditions: a cycle of 42° C. for 30 minutes, 99° C. for 5 minutes, and 55° C. for 5 minutes
2) PCR Subsequently, PCR was carried out using the obtained cDNA. PCR was carried out using the GeneAmp 9600 (Applied Biosystems) and the primers shown below (RKN, Start2×2, and PotaLRR) under the following conditions.
<PCR Utilizing Primer RKN>

Primer RKN-F1:   GTTGGTCATGAAAATGAA   (SEQ ID NO: 5)

Primer RKN-R1:   ATATTGCTCTTCCAATCA   (SEQ ID NO: 6)

TABLE 6

| Reaction composition for PCR utilizing primer RKN | |
| --- | --- |
| Substance | Amount required |
| 10x buffer | 5 μl |
| MgCl$_2$ (150 mM) | 1 μl |
| dNTP (2 mM) | 4 μl |
| Forward primer (RKN-F1, 1 pmol/(μl) | 5 μl |
| Reverse primer (RKN-R1, 1 pmol/(μl) | 5 μl |
| Taq-polymerase (10 u/ul) | 0.5 μl |
| Template | 275 ng |
| dH$_2$O | +α |
| Total | 50 μl |

Reaction condition: 30 cycles of 95° C. for 10 minutes, 95° C. for 1 minute, 55° C. for 2 minutes, and 72° C. for 3 minutes
Final elongation at 72° C. for 10 minutes
<Reaction Utilizing Primers Start2×2 and potaLRR>

Primer Start2X2:   ATGGCTTATGCTGCTATTACTTGT   (SEQ ID NO: 7)

Primer PotaLRR:   CTAACTGATACAGACCTCAACAGA   (SEQ ID NO: 8)

TABLE 7

| Reaction composition for PCR utilizing the primers Start2x2 and potaLRR | |
| --- | --- |
| Substance | Amount required |
| Buffer | 5 μl |
| MgCl$_2$ | 1 μl |
| dNTP | 4 μl |
| Forward primer (Start2x2-F, 1 pmol/μl) | 5 μl |
| Reverse primer (potaLRR-1, 1 pmol/μl) | 5 μl |
| Taq-polymerase | 0.5 μl |
| Template | 275 ng |
| dH$_2$O | +α |
| Total | 50 μl |

Figure 2:
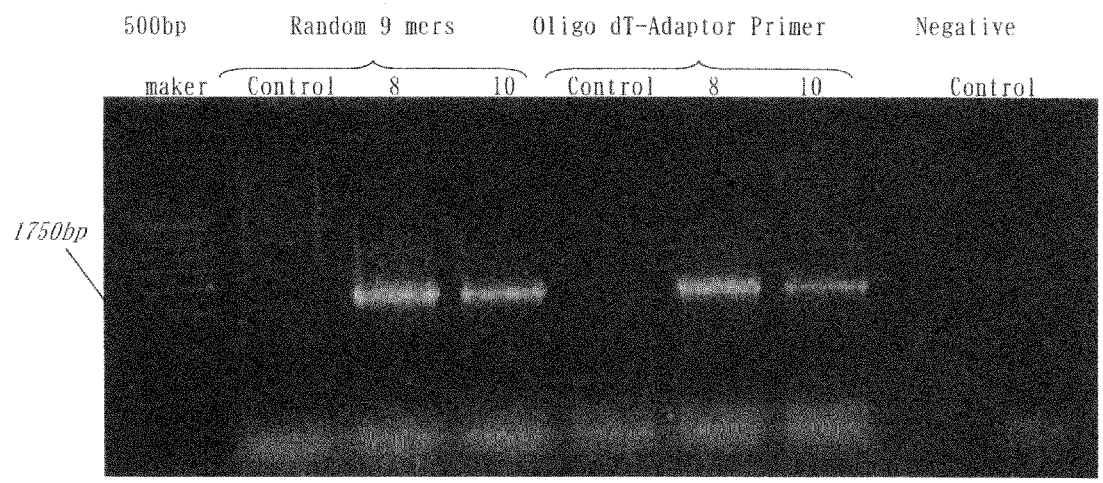
FIG. 2 shows the results of gene introduction confirmed via RT-PCR, wherein 2A represents the primer RKN, and 2B represents the primers Start2×2 and PotaLRR.
Figure 2:
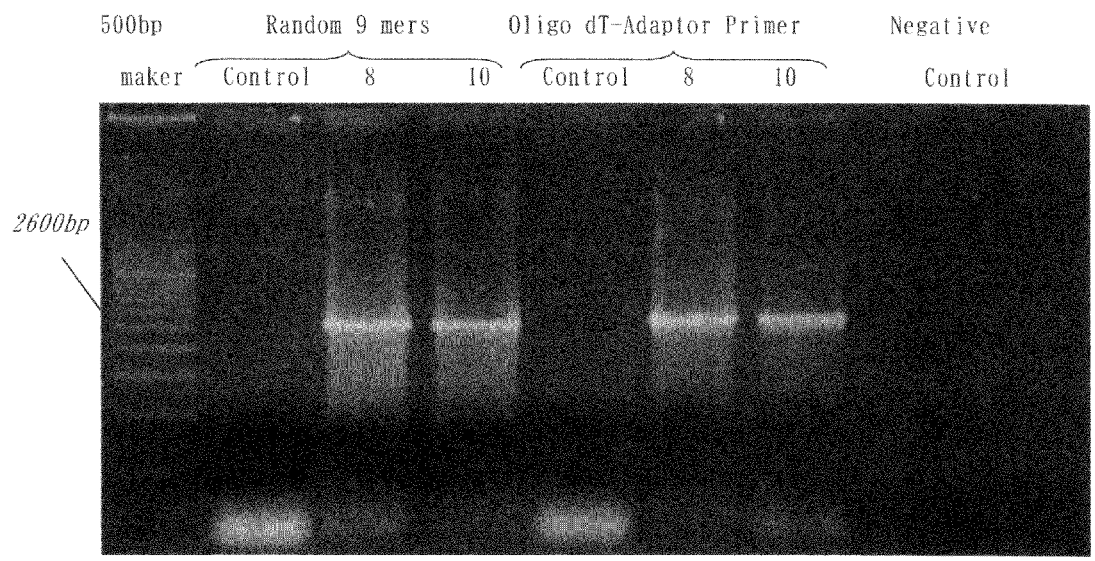

Reaction condition: 30 cycles of 95° C. for 10 minutes, 95° C. for 1 minute, 55° C. for 2 minutes, and 72° C. for 3 minutes
Final elongation at 72° C. for 10 minutes
3) Electrophoresis The PCR products obtained above were electrophoresed, and band differences thereamong were compared to evaluate the occurrence of gene introduction.
(2) Results The results of RT-PCR are shown in FIG. 2. When the primer RKN and the primers Start2×2 and PotaLRR were used, no band was observed in the control, although a band was detected in the candidates for the transgenic plant (plants 8 and 9). Thus, gene introduction to and transcription in the transgenic plants were confirmed.

Example 6

Evaluation of Resistance of Transgenic Plants (1) Testing Method

The transgenic *Nicotiana benthamiana* (e.g., Nos. 1, 8, 14, and 18), gene introduction into which had been verified, the non-transgenic *Nicotiana benthamiana*, and the nematode-sensitive tomato variety TA209 were infected with *Meloidogyne incognita*. Conditions of aerial parts and roots of the plants were observed visually and microscopically.

The transgenic *Nicotiana benthamiana* (e.g., Nos. 1, 8, 14, and 18), gene introduction into which had been verified, the non-transgenic *Nicotiana benthamiana*, and TA209 were cultivated in *Meloidogyne incognita*-infected soil to evaluate resistance. Evaluation was carried out in accordance with a conventional technique (Williamson et al., Plant Cell, 1998), root-knot nematode eggs were stained with Erioglaucine (Sigma-Aldrich), and the presence or absence and the number of eggs were examined to evaluate the resistance. At this time, the presence of galls in the roots was also examined. Thus, the correlation between the number of genes introduced and the nematode resistance was inspected.

(2) Results

Figure 3:
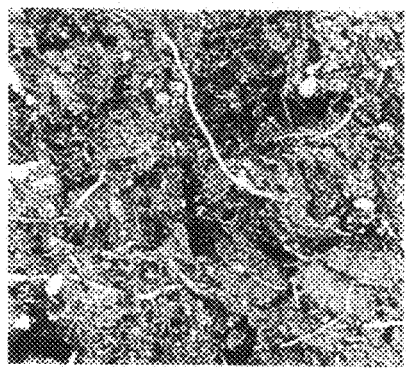
FIG. 3 is a photograph showing the conditions of the roots 42 days after root-knot nematode infection, wherein 3A represents a transgenic plant, 3B represents a control, and 3C represents TA209.
Figure 3:
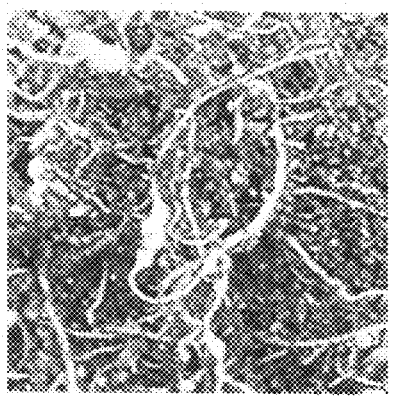
Figure 3:
Figure 4:
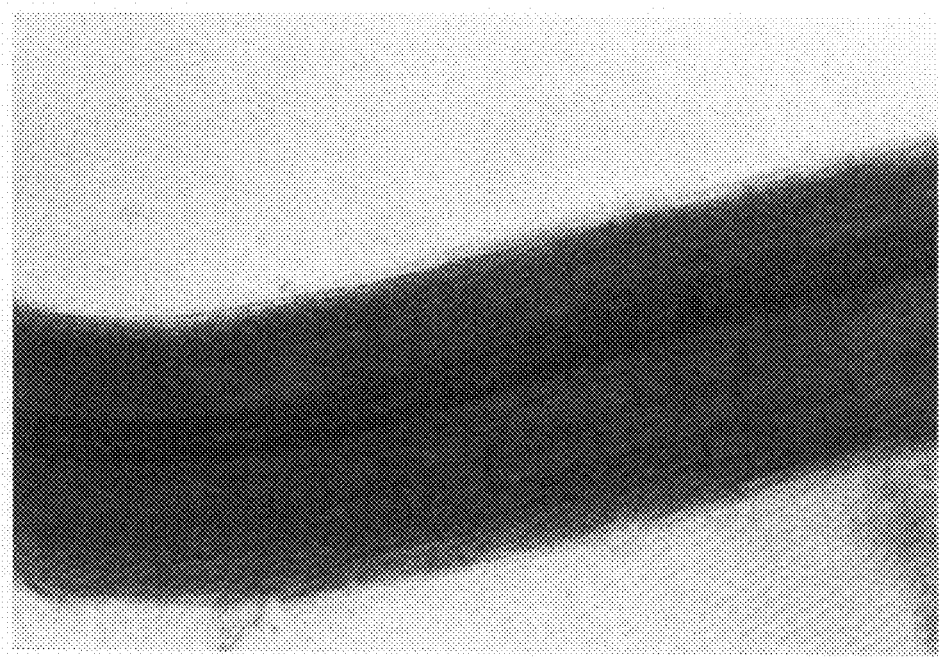
FIG. 4 is a photomicrograph (×40) showing the roots 42 days after root-knot nematode infection, wherein 4A represents a transgenic plant, and 4B represents a control.
Figure 4:

Concerning the conditions of the aerial parts of the transgenic plants, the degree of etiolation was not advanced from that of the non-transgenic plant and that of TA209. The number of root-knots was also smaller. The roots were further observed under a microscope, and knot-like deformation was not observed in the root of the transgenic plant. However, knot-like deformation was observed in the root of the non-transgenic plant and in that of TA209, and a shadow that seemed like nematode egg was observed therein. Thus, a transgenic plant into which the gene according to the present invention has been introduced was verified to have high root-knot nematode resistance (FIGS. 3 and 4).

Further, the transgenic plant according to the present invention could maintain its root-knot nematode resistance even when it was cultured and cultivated at high temperatures between 33° C. and 35° C. Accordingly, the gene according to the present invention was confirmed to be unaffected by high temperature unlike the Mi gene (which is deactivated at 28° C.).

Example 7

Evaluation of Root-Knot Nematode Resistance of Wild-Type Tobacco (1) Testing Method The nematode-resistant genes were introduced into wild-type tobacco using the vector prepared in Example 2 in accordance with the method described in Example 3. The lines into which the genes have been introduced were subjected to Southern hybridization and RT-PCR to confirm the gene introduction. Further, transgenic plants were planted in root-knot nematode-infected soil and allowed to grow in a greenhouse at 30° C. to 35° C. during the day (for 16 hours) and at 25° C. to 30° C. during the night (for 8 hours) for 6 weeks. The nematode resistance thereof was then evaluated. Resistance was evaluated by first observing the roots in terms of root knots and then microscopically observing the plants that did not have root knots. The results are shown in Table 8.

(2) Results

As is apparent from Table 8, the root-knot nematode-resistance gene according to the present invention was confirmed to have quantitative resistance unlike conventional root-knot nematode-resistance genes such as the mi gene of a tomato.

TABLE 8

| Strain | Southern hybridization Number of genes introduced | RT-PCR* | Resistance** |
|---|---|---|---|
| *N. benthamiana* | Control | N | S |
| IK-1 | I | N | S |
| IK-2 | I | N | S |
| IK-3 | I | P | MR |

TABLE 8-continued

| Strain | Southern hybridization Number of genes introduced | RT-PCR* | Resistance** |
|---|---|---|---|
| IK-4 | 3 | P | HR |
| IK-6 | 2 | P | R |
| IK-7 | 0 | — | S |
| IK-11 | 1 | P | MR |
| IK-12 | 1 | P | MR |
| IK-14 | 2 | P | R |
| IK-15 | 3 | P | HR |
| IK-16 | 0 | — | MS |
| IK-17 | 0 | — | S |
| IK-18 | 0 | — | MS |
| IK-19 | 0 | — | S |
| IK-20 | 0 | — | S |
| IK-24 | 1 | N | MS |

1) Numerical values: the number of genes introduced
I: identical to control
2) N: negative; P: positive; —: unevaluatable
3) HR: Neither root knots nor eggs were observed.
R: No root knots but some eggs were observed in roots.
MR: Some root knots and eggs were observed in roots.
MS: Many root knots were observed in roots.
S: Many root knots were observed throughout the entirety of the roots.

Example 8

Evaluation of Root-Knot Nematode Resistance of Cultivated Potato Species (1) Testing Method The nematode-resistant genes were introduced into the cultivated potato species (Desiree) using the vector prepared in Example 2 in accordance with the method described in Example 3. The species into which the genes have been introduced were subjected to Southern hybridization, PCR, and RT-PCR to confirm the gene introduction. Further, transgenic plants were planted in root-knot nematode-infected soil and allowed to grow in a greenhouse at 30° C. to 35° C. during the day (for 16 hours) and at 25° C. to 30° C. during the night (for 8 hours) for 6 weeks. The nematode resistance thereof was then evaluated in the same manner as in Example 7. As controls, untreated Desiree, root-knot nematode-sensitive Atzimba (potato), TA209, and *N. benthamiana* were allowed to grow in the same manner and then evaluated. The results are shown in Table 9.

(2) Results

As is apparent from Table 9, the root-knot nematode-resistance gene according to the present invention was confirmed to exhibit quantitative resistance in the cultivated potato species.

TABLE 9

| Line | Southern hybridization [1] Number of genes introduced | RT-PCR [2] | Resistance [3] | PCR [4] |
|---|---|---|---|---|
| Desiree | Control | N | S | N |
| RKN-2 | 2 | P | R | P |
| RKN-15 | 2 | P | R | P |
| RKN-16 | 3 | P | HR | P |
| RKN-29 | 3 | P | R | P |
| RKN-34 | 2 | P | R | P |
| RKN-36 | 3 | P | HR | P |
| RKN-37 | 2 | P | MR | P |
| RKN-38 | 2 | P | R | P |
| RKN-39 | 2 | P | R | P |
| RKN-40 | 3 | P | HR | P |
| RKN-101 | I | N | S | N |

TABLE 9-continued

| Line | Southern hybridization [1] Number of genes introduced | RT-PCR [2] | Resistance [3] | PCR [4] |
|---|---|---|---|---|
| RKN-103 | 1 | P | MR | P |
| RKN-104 | 1 | P | S | P |
| RKN-105 | 1 | P | MR | N |
| RKN-106 | I | N | S | N |
| RKN-107 | 2 | P | R | P |
| RKN-108 | 2 | P | MR | P |
| RKN-110 | 1 | P | MS | P |
| RKN-111 | 3 | P | HR | P |
| RKN-135 | 3 | P | R | P |
| Control | | | | |
| N. benthamiana | — | N | S | N |
| TA209 tomato | — | N | S | N |
| Atzimba | — | N | S | N |

[1] Numerical values: the number of genes introduced; I: the line having the same pattern as the control and the untreated line.
[2] N: negative; P: positive
[3] HR: Neither root knots nor eggs were observed.
R: No root knots but some eggs were observed in roots.
MR: Some root knots and eggs were observed in roots.
MS: Many root knots were observed in roots.
S: Many root knots were observed throughout the entirety of the roots.
[4] N: negative; P: positive All publications, patents, and patent applications cited herein are incorporated herein by reference in their entirety.

INDUSTRIAL APPLICABILITY

The present invention provides a novel root-knot nematode-resistance gene that is unaffected by high temperature and is extensively applicable to and quantitatively resistant to a wide variety of root-knot nematode species and strains. Utilization of such gene enables conferment of high root-knot nematode resistance upon major crops, such as potatoes, tomatoes, and tobacco.

Free Text of Sequence Listings
SEQ ID NO: 2: Description of artificial sequence: primer
SEQ ID NO: 3: Description of artificial sequence: primer
SEQ ID NO: 4: Description of artificial sequence: primer
SEQ ID NO: 5: Description of artificial sequence: primer
SEQ ID NO: 6: Description of artificial sequence: primer
SEQ ID NO: 7: Description of artificial sequence: primer
SEQ ID NO: 8: Description of artificial sequence: primer

The invention claimed is:

1. An isolated gene from potato, consisting of the following DNA (a) or (b):
   (a) DNA consisting essentially of the nucleotide sequence of SEQ ID NO: 1; or
   (b) DNA hybridizing under stringent conditions of 50 mM sodium and 70° C. to a nucleotide sequence complementary to SEQ ID NO: 1 and conferring root-knot nematode resistance upon a plant host, wherein the root-knot nematode resistance is unaffected by a temperature between 33° C. and 35° C.

2. The isolated gene according to claim 1, wherein the DNA confers quantitative root-knot nematode resistance, where the level of resistance increases depending on the number of gene copies in the plant host.

3. A recombinant vector comprising the isolated gene according to claim 1.

4. A transformant obtained by introducing the isolated gene according to claim 1 into a plant host.

5. The transformant according to claim 4, wherein the plant host is of the Solanaceae family.

6. A method for producing a root-knot nematode-resistant transgenic plant, said method comprising:

transforming a plant host with a vector comprising SEQ ID NO: 1.

7. An agent for root-knot nematode control comprising the isolated gene according to claim 1.

* * * * *

SEQUENCE LISTING

```
<160> NUMBER OF SEQ ID NOS: 8

<210> SEQ ID NO 1
<211> LENGTH: 2613
<212> TYPE: DNA
<213> ORGANISM: Solanum tuberosum
<220> FEATURE:
<221> NAME/KEY: misc_feature
<222> LOCATION: (110)..(110)
<223> OTHER INFORMATION: n stands for any base
<220> FEATURE:
<221> NAME/KEY: misc_feature
<222> LOCATION: (1435)..(1435)
<223> OTHER INFORMATION: n stands for any base
<220> FEATURE:
<221> NAME/KEY: misc_feature
<222> LOCATION: (2519)..(2520)
<223> OTHER INFORMATION: n stands for any base

<400> SEQUENCE: 1
atggcttatg ctgctattac ttgtcttatg agaaccatac aacaatctat tcaacttact      60
ggatgtaatt tgcaatcatt ctatgaaaag tttgaatctt tgagagcttn tttggagaaa     120
cacacgggca atcttgatgc attgaaaagc ttggaagctg aaatcataga acttgtatgc     180
actacagaag atattttgga cttggaatca agaaatgtta aaaatccaat tcaagaata      240 atagcttttt ggaaacttca ttctctcttg aaacaagcag taggacgcat tgattccacg     300
ctgaacaagt ggatggaaat gcagaacatg tacaccaaaa ggaaagatga agaagcacat     360
aacttggatc ttgctagtac tgcatcaatg tctcaacatg ttgtggagcc tcaggatatg     420
atggttggac atgaaaatga actcgagatg atcatgcagg atcagcttgc tagaggagca     480
agtgaacttg aagttgtctc cattgtaggt atgggggggca tcggtaagac aactttggct     540
gacaaaattt ataatgatcc attcataatg tcacactttg acattcgtgc aaaagctact     600
gtttcacaag agtattgcgc gaaaaatgta tgcctaagtc ttctttcttc tataagtgga     660
aagagcaatg agcatcaaga tgatgggcaa ctagctgatc gactgcaaaa aagtctaaaa     720
```

-continued

```
gggaggaggt atttagtagt cattgatgac atatggaccg aacgagcttg ggatgatatg      780
aaactatgtt tcccagattg taactgtgga agcagaatac tgctgacaac tcggaatatg      840
gaagtagcta agtatgctag ctcaggtaag cctcctaaga atcaaatgcg actcttgaat      900
attgatgaaa gttggaagtt actacccagt agagtctttg taaaaaactg tttctcccct      960
gaatttgaac aacttgggaa acaaattgct cttaaatgcg ggggattacc tttagctatt     1020
atcgttattg ctggagttct gtctaatatt ggtgagtcat ttgatgaatg acaagtgtt      1080 gcagagaatg taagttcagt ggtaagtaca gatcacaatg tacaatgcat gagagtgttg     1140
gcgttgagtt atcatcactt accacatcac ttgagagcgt gttttctata ttttgcaata     1200
ttcccggagg atacagtgat ttttgtgaat aaacttgtga aattatggac agcagagggt     1260
tttttgaaga cagaaatgat gaaagtatat gaagaagttg cagaaaaatg tgttaaagat     1320
cttatagata gaaatttagt ttttgtccaa agggtgagta gttttgatgg aaaaataaaa     1380
gcttgtggaa tgcatgatgt gatccgtgaa ctctgcttga gagaagctcg aaacncaaat     1440
tttgtgaatg ttataatgga taatcaaaat ccatgtgaac aatccatgaa ttattccaca     1500
aagggagttc ggataagtat ccaatccaaa cttgctgcca atcagttgtc tatggttgt      1560 ataacgatt cctattctgt tctcgttttt actgaagatc cctcaagctc aagaatggtg      1620
cagggcttga agcatttcaa ggtactaaga gtacttatct tgcttcggtg gcattgcatg     1680
tttcccaatt gcatagttga actatttcac ttgagatatc taggtttgag tgtttactcg     1740
tccactaatg attgggatat ttgttttcca tcctcaatag ctagccttga gtatttgcaa     1800
actttaatac ttaagtttcc aacatctctc ggatggaagt tcactagact tttcagatta     1860
ccatcgagta ttttcaagat gtcgcaattg aggcatctat cttttggactg gaattacttg    1920 aatggacatg aatctagcga gagatcaagt tgggttttga gaaatcttga gtgtctgtct     1980
ggatggaatc ctttatcttg tacttcttcg gttttttagac tacttccgaa tgtaaagaag    2040
ttgcaaatat gtggtatcca agaagactac ataagaaagg acaaggtctt tgatgatctt    2100
tgctgcttaa atcagcttac agaattgaaa tttaagatta gaaagatgat tggaagagca    2160
atatatgata catcttttgt tcttcctcct ctaggtgctt ttccgaagaa ccttaagaag    2220
ttagctttta caggtactcg tttgcattgg aaggatttgg agattcttgg taagttgcct    2280
aaactcgagg ccctcaaact aggatatgat gcctgcattg gtactgattg ggaagtaggt    2340
gaggaagggt ttccacactt gaagttcttg cgattgaagc atttgtactt gcataactgg    2400
agagctagta gtgatcattt tccacgactt gaacgactag tcattaaccg tcgttggagc    2460
atgtattcga tcccacagga ttttgtagac ataaccacac ttcagctgat tcatataann    2520
gactctgcaa aatctgttgg gaactccgcc aagaagattc agcaggaaat tgaagacagc    2580
tatggaagtt ctgttgaggt ctgtatcagt tag                                  2613
```

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 2
gatccattct ataatgtctc act    23

<210> SEQ ID NO 3
<211> LENGTH: 22

```
<212> TYPE: DNA
<213> ORGANISM: Artificial Sequence
<220> FEATURE:
<223> OTHER INFORMATION: Description of Artificial Sequence:primer

<400> SEQUENCE: 3
ctatctataa gatctttaat ca                                             22

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 4
gttttcccag tcacgac                                                   17

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 5
gttggtcatg aaaatgaa                                                  18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 6
atattgctct tccaatca                                                  18

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 7
atggcttatg ctgctattac ttgt                                           24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 8
ctaactgata cagacctcaa caga                                           24
```